(12) United States Patent
Lagarde

(10) Patent No.: US 6,443,732 B2
(45) Date of Patent: Sep. 3, 2002

(54) APPARATUS AND METHOD FOR TREATING INFECTED TOOTH USING IONOPHORESIS

(75) Inventor: Philippe Lagarde, La Salute di Livenza (IT)

(73) Assignee: Barston International Ltd., Geneva (CH)

( * ) Notice: Subject to any disclaimer, the term of this patent is extended or adjusted under 35 U.S.C. 154(b) by 0 days.

(21) Appl. No.: 09/805,466

(22) Filed: Mar. 14, 2001

(30) Foreign Application Priority Data

Mar. 16, 2000 (CH) .............................................. 0499/00

(51) Int. Cl.⁷ ................................................. A61C 5/02

(52) U.S. Cl. ........................................ 433/224; 433/32

(58) Field of Search ................................... 433/32, 224

(56) References Cited

U.S. PATENT DOCUMENTS

| | | | | |
|---|---|---|---|---|
| 1,312,270 A | * | 8/1919 | Russell ......................... | 433/32 |
| 2,121,875 A | * | 6/1938 | Kruse et al. .................. | 433/32 |
| 2,465,838 A | | 3/1949 | Bernard ....................... | 363/34 |
| 3,842,841 A | * | 10/1974 | Brighton et al. ............ | 128/419 |
| 4,993,947 A | | 2/1991 | Grosrey ....................... | 433/81 |

FOREIGN PATENT DOCUMENTS

| | | |
|---|---|---|
| CH | 257243 | 4/1949 |
| FR | 916843 | 12/1946 |

OTHER PUBLICATIONS

Bernard, "Rapid and Radical Treatment of the Pulpa Tissues and Periapical Affections Using the New Methods of Ionophoresis and Diadynamic Therapy" (11 trattamento rapido e radicale delle gengive pulpari e delle affezioni periapicali mediante 1 nuovi metodi di ionoforesi e die terapia diadi–namica), published and edited by the Physiotechnie SA (Company), Paris, (1992).

Lagarde et al., "Treatment of Infected Teeth" (Trattamento dei denti infetti), a study published sometime after 1974 in France by the Imprimeriex Company, 51bis Av. de Pessicart, Nice.

* cited by examiner

Primary Examiner—John J. Wilson
(74) Attorney, Agent, or Firm—Greenblum & Bernstein, P.L.C.

(57) ABSTRACT

Apparatus and method for treating a tooth infected by a pathogen. The apparatus comprises at least one adjustable electric voltage generator for generating an direct current, an applicator device having a first pole and a second pole, the first pole being formed as a needle so as to penetrate into a canal of the infected tooth and the second pole being brought into direct contact with a zone of a body of a patient having the infected tooth and an electric circuit for maintaining the direct current constant while an impedance of the at least one adjustable electric voltage generator varies, the impedance being determined by the zone of the body of the patient where the direct current passes.

The method for treating a tooth infected by a pathogen comprises applying an direct current into a canal of the infected tooth and maintaining the direct current constant during a duration of an application of the direct current to the infected tooth.

21 Claims, 1 Drawing Sheet

APPARATUS AND METHOD FOR TREATING INFECTED TOOTH USING IONOPHORESIS

CROSS-REFERENCE TO RELATED APPLICATIONS

The present application claims priority under 35 U.S.C. § 119 of Swiss Patent Application No. CH 2000 0499/00, filed on Mar. 16, 2000, the disclosure of which is expressly incorporated by reference herein in its entirety.

BACKGROUND OF THE INVENTION

1. Field of the Invention

The present invention relates to an apparatus for sterilization or treatment, using ionophoresis, of the canals of a tooth infected by pathogens. The present invention relates to a method for sterilization or treatment, using ionophoresis, of the canals of a tooth infected by pathogens.

2. Discussion of Background Information

The principle of treating an infected tooth using ionophoresis is known. See P. D. Bernard, "Rapid and Radical Treatment of the Pulpa Tissues and Periapical Affections Using the New Methods of Ionophoresis and of Diadynamic Therapy" (Il trattamento rapido e radicale delle gengive pulpari e delle affezioni periapicali mediante l nuovi metodi di ionoforesi e die terapia diadi-namica), which was published and edited by the Physiotechnie SA (Company), Paris, (1929), and Ph. Lagarde and R. P. Lagarde, "Treatment of Infected Teeth" (Trattamento dei denti infetti), a study published sometime after 1974 in France by the Imprimeriex Company, 51bis Av. de Pessicart, Nice. The Lagarde study cites a large bibliography concerning various methods of treating dental infections among which is included a method for using ionophoresis. These publications illustrate devices or apparatuses, which are useful for ionophore treatment; however, the publications do not describe the present inventive apparatus or method. Rather, the publications give some general indications which do not provide anything other than a general knowledge concerning the formation of "OH" ions penetrating the "aberrant" canals of the teeth.

French patent 916843 describes an apparatus and method useful in medical or dentistry electrotherapy comprising supplying direct current to a circuit, the output current of the circuit being regulated by two potentiometers. The direct current is superimposed with a source of low voltage alternating current, the voltage of which can be regulated by another potentiometer which is pre-set not as a function of the voltage it supplies but rather is set in such a manner for obtaining an optimum analgetic effect with respect to the intensity of the direct current supplied. In other words, an alternating current is applied to the direct current such that the alternating current is superimposed as a low frequency sine differential with a potential of 5 volts, thus providing an anaesthetic action when it is superimposed to an externally supplied direct current of 1 milliamp. However, if this same 5 volt ac voltage is applied to a direct current of 3 or 4 milliamps, its action upon the sensitivity predominates, and becomes intolerable with a direct current intensity of 5 milliamps.

FR 916843 teaches a method for electro-therapeutic dentistry treatment where an anaesthetic effect is obtained. This anesthetic effect is different from the present invention which is directed to a method of sterilization (and thus of disinfection) of the canals of the tooth treated using ionophoresis. Furthermore, FR 916843 also states that in some cases the direct current is tolerated badly, when an alternating current is superimposed thereon. Thus, FR 916843 does not teach the use of ionophoresis as a therapeutic method for treating a tooth infected with a pathogen and does not teach an apparatus suitable for implementing the inventive therapeutic method.

CH-257243 teaches an electrotherapeutic apparatus for permitting the generation of a modulated current of a frequency of a plurality of seconds as desired and a syncope current of short periods, the apparatus being useful for the treatment of pain, for the treatment of atonicity and for the diagnosis of neuro-muscular disorders by applying a modulated current, which is generated by thermoionic valves co-operating with interrupt relays. On the other hand, the apparatus of the present invention is structurally different from the apparatus of CH-257243 and the method of the present invention is used for a different utility, treating a tooth infected by a pathogen. It should be noted that an apparatus described in the Ph. And R. P. Lagarde study, page 29, uses two poles, namely, a negative electrode and a positive electrode. The negative electrode is a metallic probe which is shaped as a needle so as to penetrate into the depth of a canal of the tooth to be treated, whereas the positive electrode is brought into direct contact with a body zone of the patient and preferably shaped as a metallic cylinder which the patient holds in his hand.

The use of an alternating current in other apparatus, as well as other electrophoretic methods, predominantly generates an anaesthetizing effect rather than a sterilizing effect. To obtain an anaesthetizing effect, it is necessary to make sure that after a positive current impulse a negative impulse follows, as the anaesthetizing effect is based on the decoding of the nerve ends. This mechanism of anaesthesia does not yield satisfactory results. For this reason, the anaesthetizing effect of the ionophoretic treatment is not used today.

SUMMARY OF THE INVENTION

The present invention relates to an apparatus for treating a tooth infected by a pathogen and to a method for treating a tooth infected by a pathogen. The present invention provides for the application of a direct current rather than an alternating current, which is different from other practice and teachings. To obtain the desired treatment, e.g., a disinfection effect or sterilization, it is sufficient to apply a direct current which advantageously can be metered easily in its timing. Furthermore, a direct current can be applied at lower voltage and over shorter time periods than an alternating current, thereby resulting in a reduction of the dangers and of the total application time.

The present invention provides an apparatus for sterilizing a tooth using ionophoresis and provides optimum characteristics for obtaining the sterilizing effect within the shortest possible time and eliminates the disadvantages of other devices. In other apparatus, it has been found that the applied electric current is varied and that there are variations in the circuit impedance Z. The variation in the impedance in a circuit in which one of the poles directly contacts the skin of the patient has many causes, the main one being the variation in humidity of the skin tissue caused by sweating.

The variations in the impedance of the circuit are likely caused by physiologic effects, which are uncontrollable and are foreseeable by the operator. These variations greatly impair the constancy of the current applied, thus rendering control of the working method difficult and endangering the good result of the treatment. The present invention obviates the aforementioned problems and thus enables treatment of a patient despite the local physiologic conditions of the patient.

In accordance with an embodiment of the present invention, the apparatus applies an electric current as a direct current and the direct current is generated by an adjustable generator which normally supplies the current at a maximum voltage of about 89 volts. The apparatus also has an electric circuit which maintains the direct current constant as the impedance Z of the circuit varies by taking into account the fact that impedance Z essentially is determined by the skin tissue of the body zone of the patient, normally a hand, through which the current passes.

The apparatus and method of the present invention have advantages over other apparatus and methods, namely, the speed of the treatment, the reduction of risks owing to the reduced voltage of the applied current and the ability to control the treatment free from the influence of uncontrollable parameters, such as sweat secretion of the patient, the degree of humidity of the air in the surrounding room, etc.

In another preferred embodiment of the present invention, the apparatus may comprise a programmable microprocessor, which monitors and controls all functions of the apparatus.

The present invention relates to an apparatus for treating a tooth infected by a pathogen comprising: at least one adjustable electric voltage generator for generating direct current; an applicator device having a first pole and a second pole, the first pole being formed as a needle so as to penetrate into a canal of the infected tooth and the second pole being brought into direct contact with a zone of a body of a patient having the infected tooth; and an electric circuit for maintaining the direct current constant while an impedance of the at least one adjustable electric voltage generator varies, the impedance being determined by the zone of the body of the patient where the direct current passes.

In the apparatus, the direct current has a voltage of not more than about 89 volts and the apparatus may also comprise a second electric circuit for limiting an amperage of the direct current below about 5 mA.

The apparatus can further comprise a timer for pre-setting a time duration of an application of the direct current to the patient being treated. The apparatus can further comprise a control device for controlling the amperage of the direct current, the control device and the timer being capable of manual operation.

In another embodiment, the apparatus can further comprise a programmable microprocessor for monitoring and controlling all functions of the apparatus. The programmable microprocessor can have a safety arrangement which permits the start of an ionophoresis treatment after an operator has confirmed that the tooth to be treated has been subject to a satisfactory anaesthesia by the operator effecting a suitable pain test. The safety arrangement can comprise an electric test discharge emitter circuit.

The present invention also relates to a method for treating a tooth infected by a pathogen comprising: applying direct current into a canal of the infected tooth and maintaining the direct current constant during a duration of an application of the direct current to the infected tooth. The direct current can have a current voltage of not more than about 89 volts and an amperage of the direct current below about 5 mA.

In the method, the duration of an application of the direct current to the patient being treated is dependent upon the amperage of the direct current, a time of application of the direct current, a position in the dental arc of the tooth being treated and a pathology of the tooth. The duration of an application of the direct current to the patient being treated can be determined by taking into consideration the product of the amperage of the direct current and the time of application of the direct current.

In the method, the amperage of the direct current is controlled by an operator.

In another embodiment of the method, a programmable microprocessor can be used which monitors and controls the amperage of the direct current and the time duration of the application of the direct current.

In the method, the treatment is started after an operator has confirmed that the tooth to be treated has been subject to a satisfactory anaesthesia by the operator effecting a suitable pain test.

In the method, the quantity of direct current applied to the infected tooth can range from about 100 to about 1000 mAsec, and preferably from about 200 to about 500 mAsec.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the drawing by way of non-limiting examples of exemplary embodiments of the present invention, and wherein:

The FIGURE illustrates an apparatus for treating a tooth infected by a pathogen.

DETAILED DESCRIPTION OF THE PRESENT INVENTION

Figure 1:
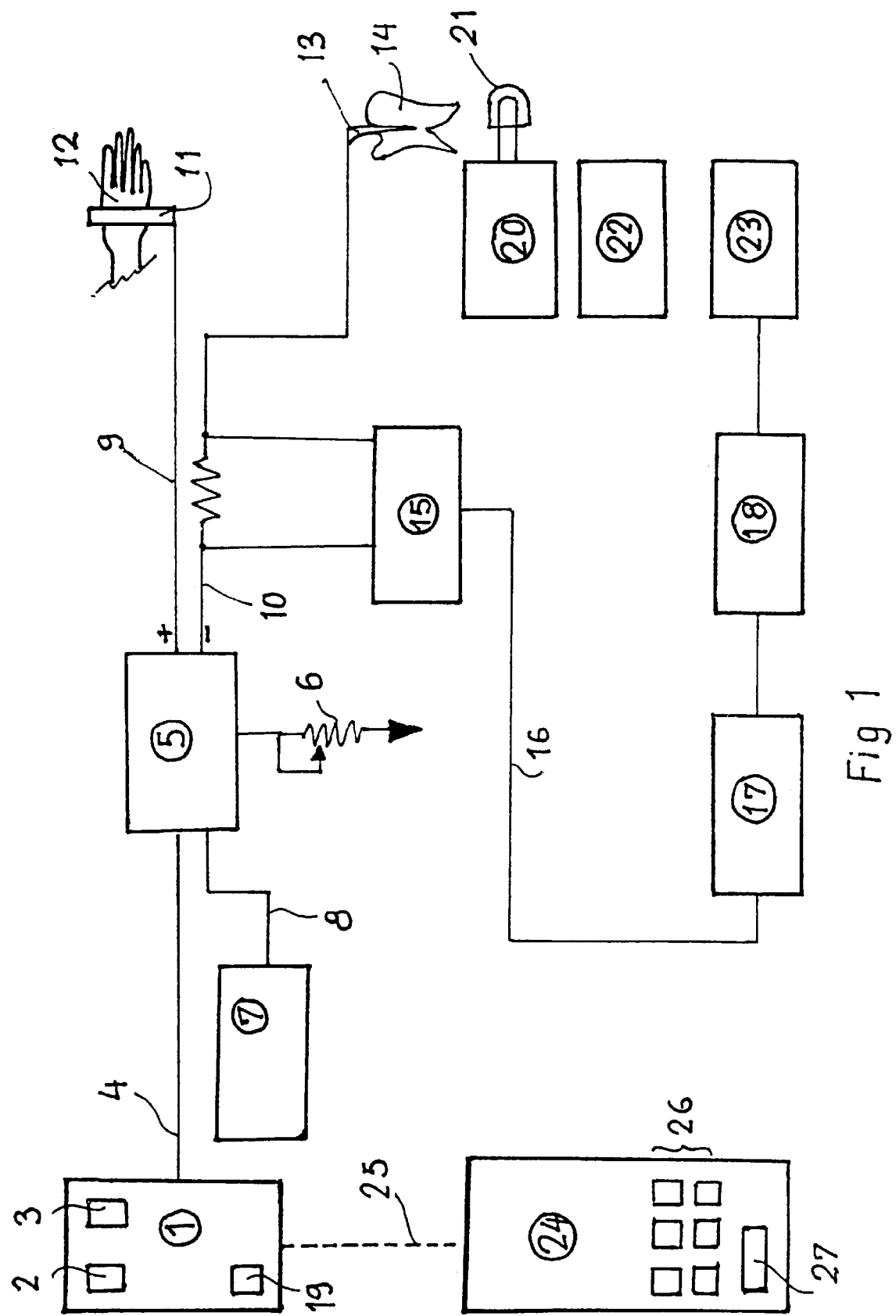

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The FIGURE illustrates a block diagram of an apparatus for implementing the present invention, which diagram is explained below.

Box 1 is a manual control panel, which contains at least one push button 2 for starting the apparatus (start) and push button 3 for stopping the apparatus (stop). The control panel is connected via circuit line 4 with electric circuit 5 for maintaining constant the direct current. Operably attached to electric circuit 5 is regulator 6, which an operator can use to adjust the direct current and to maintain the direct current constant over time, even if the contacting points (handle 11 held in the hand 12 of the patient, and probe 13 in the root canal of the tooth) change the physical characteristics of conductivity. While the negative electrode is a metallic probe, the probe may be of any convenient shape, such as a needle, cylinder, cone or the like, so long as the probe is capable of penetrating into the depth of a canal of the tooth to be treated. Electric circuit 5 delivering the constant direct current is supplied with direct current by voltage generator 7, which is supplied with current from a grid or a battery, not shown. Voltage generator 7 generates a voltage of not more than about 80 volts at the maximum (for safety reasons prescribed by law) and exerts control such that the amperage of the direct current does not exceed 5 mA. Voltage generator 7 supplies the electric circuit 5 via electric line 8. From electric circuit 5 extend electric lines 9 and 10. Electric line 9 corresponds to the positive pole and extends to handle 11 which the patient presses in his hand 12. Handle 11 is exemplary and in lieu of the handle any other element, such as a cylinder, a conductive hand or wrist wrap, a conductive glove, a conductive place mat upon which the hand rests, etc., which is capable of providing direct contact with the patient, in particular between a zone of the skin and electric line 9, may be used.

Electric line 10 (which corresponds to the negative pole) extends to needle 13 which is inserted for the treatment in a cavity which has been previously drilled out in tooth 14 in such a manner that the method for treating (disinfecting) the tooth using ionophoresis may be performed on the canals of tooth 14. The drilling operation is performed by a dentist in the normal manner for drilling out decay in a tooth.

Electric line 10 is operably connected to current sensor 15 which ensures continuity of the electric circuit by emitting an electric signal via line 16 to detector 17, which scans the on/off state of the circuit. Detector 17 in turn controls current integrator 18 which continually effects the multiplication of the intensity of the current applied, measured in mA, with the duration of the application time according to a preferred embodiment of the present invention. Control panel 1 contains timer 19, which, according to a preferred embodiment of the present invention, an operator can pre-set for the time duration of the application of current for each single treatment of sterilization of the tooth. In the simplest lay-out of the inventive apparatus, the operator can determine the settings through routine experimentation and/or with the help of tables, such as Table 1, indicating the intensity of the current to be applied with respect to the type of pathology of the tooth to be treated, taking into consideration the position of the tooth in the dental arc. Also for this operation the operator can use of experimentally established nomograms that, however, are not object of the present invention.

In a further embodiment of the present invention, the apparatus may further comprise detector 20, Amp meter 22 and Coulomb meter 23. Detector 20 detects a threshold current intensity (set e.g. at about 4 mA) and has LED 21 for indicating that the maximum current intensity (about 5 mA) is almost reached. An amperage greater than a pre-set maximum current intensity (about 5 mA as a rule) is to be avoided. Amp meter 22 and Coulomb meter 23 measure the current intensity in mA and are optional elements of the present invention. These additional elements represent precautionary safety elements that increase the security of the treatment.

In a further embodiment of the present invention, the apparatus need not have control panel 1, but rather has programmable microprocessor 24, which permits monitoring and control of all the functions of the inventive apparatus. As can be seen in the FIGURE, programmable microprocessor 24 is connected via a line 25 indicated in cashed lines (which signifies that programmable microprocessor 24 represents an alternative solution).

In accordance with a preferred embodiment of the present invention, the apparatus contains programmable microprocessor 24 for monitoring and controlling the maximum voltage (e.g., about 80 volts) of the direct current generated by voltage generator 7 and for monitoring and controlling electric circuit 5 in order to maintain the direct current constant while impedance Z of the circuit varies (possibly due to the variation in electric conductivity between hand 12 of the patient and handle 11). Also programmable microprocessor 24 can monitor and control the time duration of treatment by calculating the product of the intensity of the current applied with the time duration of application as a function of the position of the tooth to be treated in the dental arc and of the pathology to be treated.

In accordance with a preferred embodiment of the present invention, the success of the disinfection treatment of the tooth using ionophoresis depends upon the time duration of the application of the electric current by taking into consideration that the product of the regulated intensity of the current, measured in mA, with the duration of application, measured in seconds together with the position in the dental arc of the tooth to be treated and on the pathology of the tooth itself. These relationships are based upon empirical observations, which can be determined by routine experimentation, from a number of treatments. These observations are not part of the present invention.

In another embodiment of the present invention, programmable microprocessor 24 can be provided with keyboard 26, which an operator can program and/or type all data to be fed into the microprocessor, which data is required for realizing any specific type of treatment using ionophoresis.

In accordance with another further preferred embodiment of the present invention, the microprocessor can be provided with safety arrangement 27, which allows the start of the desired treatment using ionophoresis only after confirmation by the operator that the tooth to be treated has been subject to a satisfactory anaesthesia which the operator checks by applying a suitable pain test. The purpose of this safety arrangement is self-evident—the treatment of the canals of a tooth using ionophoresis can be painful if the tooth has not been properly anaesthetized previously. For this operation chemical anaesthesia is preferred and is applied via injection to the canals. It is to be noted here that neither the operation of preparing the dental canals (opening by trepanning, elimination of the nerve) nor the anaesthesia in any way constitutes any obstacle to the application of the inventive apparatus.

In another preferred embodiment of the present invention, safety arrangement 27 can be provided with a structural element (not shown) for emitting an electric test discharge that can be regulated by the operator who can make sure that the tooth to be treated has been subject to an anaesthesia that is satisfactory for the predetermined conditions for the planned ionophoresis treatment. Because of this additional arrangement the operator, after having prepared the canal of the tooth, having applied a chemical anaesthesia by injection, and having extracted the nerve, can easily make sure without loosing time that the anaesthesia still is effective. In other words, the anaesthesia is effective to such an extent that the sterilization treatment using ionophoresis to which the patient will be subsequently subjected will be painless and the treatment can have a duration of several minutes and longer.

In another preferred embodiment of the present invention, the quantity of electric direct current supplied by voltage generator 7 during a treatment of sterilization using ionophoresis, measured in mAsec, ranges between 100 and 1000 mAsec, and more precisely between 200 and 500 mAsec. This indication serves for determining and laying out the dimensions of the electric lines and circuits according to the FIGURE.

The apparatus illustrated in the FIGURE is not the only configuration suitable for making the inventive apparatus. In a general form, it is sufficient if voltage generator 7 is provided which supplies a continuous voltage, and electric circuit 5 which maintains the direct current constant independently of the varying impedance Z of the electric circuit. The other devices described serve for facilitating the task of the operator and in particular for enhancing the operating safety and for avoiding any danger of occurrence of pain in the patient due to a ionophoresis treatment of the dental canals which is excessively intense.

Secondary electric circuits forming the various components of block diagram 1 such as programmable microprocessor 24 are well known to those skilled in the art and comprise elements readily available in the market. Thus a further description of the electric circuits of the individual components and a more detailed discussion of the electric circuit of the inventive apparatus is not necessary.

For the application of the apparatus of the present invention, however, the application nomograms are most important which contain the relationships between the position of the teeth in the dental arc, the pathology to be treated and the intensity of the ionophoresis treatment required for obtaining the desired results. Table 1 represents an example of the relationship between the pathology of the tooth and the quantity of direct current to be applied. Of course, the operator using the inventive apparatus must have similar information at his disposal, which he can determine by routine experimentation based on his own personal experience or on the experiences of other specialists in order to make best use of the inventive apparatus. Such information to a great extent can be programmed, if microprocessor 24 is incorporated in the apparatus, and thus always is at the disposal of the operator who only has to select the general parameters (tooth to be treated, pathology) for safely using the inventive apparatus. This presents the possibility of adopting a so-called expert system (software program) on microprocessor 24.

Table 1 contains seven examples, which show the interdependence between the pathology of the tooth to be treated and the amount of electric direct current to be applied. It should be understood that the examples are exemplary, since each example shows the intensity of the current to be applied. The results also depend on the time duration of the application for each individual sterilizing treatment, i.e., the product of amperage of the direct current in milliamps (mA) and the time of the duration of the direct current in seconds, as well as the pathology of the tooth to be treated and the position of the tooth within the dental arc. The operator of the apparatus can determine the interdependence by routine experimentation.

TABLE 1

| 1 | Canal without infection live pulp | 2 Decicoulombs per Canal with probe length ≧ ⅔ of Canal length 3 Decicoulombs per Canal with probe length < ⅔ of Canal length Pyorrhea = 3 Decicoulombs |
|---|---|---|
| 2 | Canal infected live pulp | 3 Decicoulombs per Canal |
| 3 | Canal pulp disappeared with or without pus | 4 Decicoulombs per Canal |
| 4 | Cellulite | 5 Decicoulombs per Canal |
| 5 | Granuloma without infection | 4 Decicoulombs per Canal |
| 6 | Granuloma infected | 5 Decicoulombs per Canal |
| 7 | Through metal pin | 4 Decicoulombs per Canal |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF THE ELEMENTS REFERRED TO IN THE FIGURE

1 Manual control panel
2 Start button
3 Stop button
4 Electric line
5 Electric circuit maintaining the direct current constant
6 Regulator
7 Voltage generator
8 Electric line
9 Electric line
10 Electric line
11 Handle
12 Hand
13 Probe
14 Tooth
15 Current sensor
16 Electric line
17 Detector of on/off state of the circuit
18 Current integrator
19 Timer
20 Detector for the threshold intensity of the current
21 LED (light emitting diode)
22 Amp meter
23 Coulomb meter
24 Programmable microprocessor
25 Electric line
26 Keyboard
27 Safety arrangement

What is claimed is:

1. An apparatus for treating a tooth infected by a pathogen comprising:

at least one adjustable electric voltage generator for generating direct current;

an applicator device having a first pole and a second pole, the first pole being formed as a probe so as to penetrate into a canal of the infected tooth and the second pole being brought into direct contact with a zone of a body of a patient having the infected tooth; and an electric circuit for maintaining the direct current constant while an impedance of the at least one adjustable electric voltage generator varies, the impedance being determined by the zone of the body of the patient where the direct current passes.

2. The apparatus of claim 1 wherein the direct current has a voltage of not more than about 89 volts.

3. The apparatus of claim 1 wherein the direct current has a voltage of not more than about 89 volts and further comprising a second electric circuit for limiting an amperage of the direct current below about 5 mA.

4. The apparatus of claim 1 further comprising a timer for pre-setting a time duration of an application of the direct current to the patient being treated.

5. The apparatus of claim 4 further comprising a control device for controlling the amperage of the direct current, the control device and the timer being capable of manual operation.

6. The apparatus of claim 1, further comprising a programmable microprocessor for monitoring and controlling all functions of the apparatus.

7. The apparatus of claim 6, wherein the programmable microprocessor has a safety arrangement which permits the start of an ionophoresis treatment after the tooth to be treated has been subject to a satisfactory anaesthesia.

8. The apparatus of claim 7, wherein the safety arrangement comprises an electric test discharge emitter circuit.

9. The apparatus of claim 8, wherein the quantity of direct current applied to the infected tooth ranges from about 100 to about 1000 mAsec.

10. The apparatus of claim 9, wherein the quantity of direct current applied to the infected tooth ranges from about 200 to about 500 mAsec.

11. The apparatus of claim 1, wherein the first pole is formed as a needle.

12. A method for treating a tooth infected by a pathogen comprising:
applying direct current into a canal of the infected tooth and maintaining the direct current constant during a duration of an application of the direct current to the infected tooth.

13. The method of claim 12 wherein the direct current has a voltage of not more than about 89 volts.

14. The method of claim 12 wherein the direct current has a current voltage of not more than about 89 volts and an amperage of the direct current below about 5 mA.

15. The method of claim 12 wherein the duration of an application of the direct current to the patient being treated is dependent upon the amperage of the direct current, a time of application of the direct current, a position in the dental arc of the tooth being treated and a pathology of the tooth.

16. The method of claim 12 wherein the duration of an application of the direct current to the patient being treated is determined by taking into consideration the product of the amperage of the direct current and the time of application of the direct current.

17. The method of claim 12, wherein the amperage of the direct current is controlled by an operator.

18. The method of claim 12, wherein a programmable microprocessor monitors and controls the amperage of the direct current and the time duration of the application of the direct current.

19. The method of claim 12, wherein the treatment is started after an operator has confirmed that the tooth to be treated has been subject to a satisfactory anaesthesia by the operator effecting a suitable pain test.

20. The method of claim 12, wherein the quantity of direct current applied to the infected tooth ranges from about 100 to about 1000 mAsec.

21. The method of claim 20, wherein the quantity of direct current applied to the infected tooth ranges from about 200 to about 500 mAsec.

* * * * *